(12) United States Patent
Tasaka

(10) Patent No.: US 8,877,821 B2
(45) Date of Patent: Nov. 4, 2014

(54) METHOD AND SYSTEM FOR SYNTHESIZING LIQUID HYDROCARBON COMPOUNDS

(75) Inventor: Kazuhiko Tasaka, Tokyo (JP)

(73) Assignees: Japan Oil, Gas and Metals National Corporation, Tokyo (JP); INPEX Corporation, Tokyo (JP); JX Nippon Oil & Energy Corporation, Tokyo (JP); Japan Petroleum Exploration Co., Ltd., Tokyo (JP); Cosmo Oil Co., Ltd., Tokyo (JP); Nippon Steel Engineering Co., Ltd., Tokyo (JP)

( * ) Notice: Subject to any disclaimer, the term of this patent is extended or adjusted under 35 U.S.C. 154(b) by 449 days.

(21) Appl. No.: 13/138,675

(22) PCT Filed: Mar. 17, 2010

(86) PCT No.: PCT/JP2010/001896
§ 371 (c)(1),
(2), (4) Date: Sep. 15, 2011

(87) PCT Pub. No.: WO2010/109813
PCT Pub. Date: Sep. 30, 2010

(65) Prior Publication Data
US 2012/0010304 A1    Jan. 12, 2012

(30) Foreign Application Priority Data
Mar. 27, 2009   (JP) ................ 2009-080490

(51) Int. Cl.
| | | |
|---|---|---|
| C07C 27/00 | (2006.01) |
| C01B 3/52 | (2006.01) |
| C10K 1/00 | (2006.01) |
| C10G 65/14 | (2006.01) |
| C10G 2/00 | (2006.01) |
| C10G 65/04 | (2006.01) |
| C10G 45/02 | (2006.01) |
| C10K 1/08 | (2006.01) |
| C10G 47/00 | (2006.01) |
| B01D 53/77 | (2006.01) |
| C10K 1/14 | (2006.01) |

(52) U.S. Cl.
CPC ... *C10G 2/32* (2013.01); *C01B 3/52* (2013.01); *C10K 1/005* (2013.01); *C10G 2400/06* (2013.01); *C10G 2400/08* (2013.01); *C10G 65/14* (2013.01); *C01B 2203/0233* (2013.01); *C10G 2400/02* (2013.01); *C01B 2203/062* (2013.01); *B01D 53/77* (2013.01); *C10G 2/30* (2013.01); *B01D 2257/504* (2013.01); *C10G 65/04* (2013.01); *C01B 2203/0415* (2013.01); *C10G 2/342* (2013.01); *C10G 45/02* (2013.01); *C01B 2203/148* (2013.01); *C01B 2203/043* (2013.01); *C01B 2203/0894* (2013.01); *C01B 2203/047* (2013.01); *C01B 2203/146* (2013.01); *C10K 1/143* (2013.01); *C10K 1/08* (2013.01); *C01B 2203/0811* (2013.01); *C01B 2203/0475* (2013.01); *C10G 2/344* (2013.01); *C10G 2400/04* (2013.01); *C10G 47/00* (2013.01); *C10G 2300/1022* (2013.01)
USPC .......................................... 518/700; 518/728

(58) Field of Classification Search
USPC .................................... 518/700, 728
See application file for complete search history.

(56) References Cited

U.S. PATENT DOCUMENTS

| 6,774,148 | B2 | 8/2004 | O'Rear | |
|---|---|---|---|---|
| 2004/0157938 | A1 | 8/2004 | Iwamoto et al. | |
| 2004/0220443 | A1* | 11/2004 | De Graaf et al. | ............ 585/943 |

FOREIGN PATENT DOCUMENTS

| CN | 101210186 | 7/2008 |
|---|---|---|
| CN | 101270297 | 9/2008 |
| JP | 2003-105344 | 4/2003 |
| JP | 2004-323626 | 11/2004 |
| JP | 2005-211878 | 8/2005 |
| JP | 2005-530892 | 10/2005 |
| WO | 2004/080573 | 9/2004 |

OTHER PUBLICATIONS

International Search Report dated Apr. 13, 2010 issued in corresponding PCT Application No. PCT/JP2010/001896.
European Search Report, dated Sep. 7, 2012, issued in corresponding European Application No. EP 10755616.9.
C. Gomez et al.: "Simulation of an Industrial Packed Column for Reactive Absorption of C02", Latin American Applied Research, vol. 33, Dec. 31, 2003, pp. 201-205.
J. de Hullu et al.: "Comparing different biogas upgrading techniques: Final report," Eindhoven University of Technology, Jul. 3, 2008, pp. FP-52.
Chinese Office Action dated Jun. 20, 2013 issued in corresponding Chinese Application No. 2010800130861 (with English Translation).

* cited by examiner

*Primary Examiner* — Jafar Parsa
(74) *Attorney, Agent, or Firm* — Kenyon & Kenyon LLP

(57) ABSTRACT

Provided is a method for synthesizing liquid hydrocarbon compounds wherein synthesizing liquid hydrocarbon compounds from a synthesis gas by a Fisher-Tropsch synthesis reaction. The method includes a first absorption step of absorbing a carbon dioxide gas, which is contained in gaseous by-products generated in the Fisher-Tropsch synthesis reaction, with an absorbent, and a second absorption step of absorbing a carbon dioxide gas, which is contained in the synthesis gas, with the absorbent which is passed through the first absorption step.

8 Claims, 3 Drawing Sheets

METHOD AND SYSTEM FOR SYNTHESIZING LIQUID HYDROCARBON COMPOUNDS

TECHNICAL FIELD

The present invention relates to a method and a system for synthesizing liquid hydrocarbon compounds.

This application is a national stage application of International Application No. PCT/JP2010/001896, filed Mar. 17, 2010, which claims priority to Japanese Patent Application No. 2009-080490, filed Mar. 27, 2009, the content of which is incorporated herein by reference.

BACKGROUND ART

As one of the methods for synthesizing liquid fuels from natural gas, the GTL (Gas To Liquids: liquid fuels synthesis) technique is known. The GTL technique is a technique of producing liquid fuel products, such as naphtha (raw gasoline), kerosene, gas oil, and wax, through the steps of reforming a natural gas to produce a synthesis gas containing a carbon monoxide gas (CO) and a hydrogen gas ($H_2$) as main components, synthesizing hydrocarbon compounds (hereinafter also refereed to as "FT synthesis hydrocarbons") using this synthesis gas as a feedstock of the Fischer-Tropsch synthesis reaction (hereinafter also referred to as "FT synthesis reaction"), and hydrogenating and fractionally distilling the FT synthesis hydrocarbons. The liquid fuel products using the FT synthesis hydrocarbons as a feedstock have high paraffin content, and do not include sulfur components, for example, as shown in Patent Document 1, the liquid fuel products have attracted attention as environment-friendly fuels.

As techniques of reforming natural gas, for example, reforming methods using carbon dioxide gas, such as steam and carbon dioxide gas reforming method and a carbon dioxide gas reforming method, are known. In case of reforming a natural gas using the carbon dioxide gas, an unreacted carbon dioxide gas is contained in the synthesis gas in a relatively high concentration. Therefore, a step of separating the carbon dioxide gas from the synthesis gas before the FT synthesis reaction may be adopted. The separated carbon dioxide gas is reused for reforming the natural gas.

In the FT synthesis reaction, heavy FT synthesis hydrocarbons with a relatively large carbon number are produced as a liquid, and various kinds of gases are generated as gaseous by-products. In the gaseous by-products, for example, a carbon dioxide gas, steam, hydrocarbon compounds with a carbon number of two or less, and hydrocarbon compounds with a carbon number of three or more are included. The gaseous by-products are discharged along with unreacted synthesis gas from a synthesis reactor which performs FT synthesis reaction. The discharged gaseous by-products are introduced into a separator and condensed light liquid hydrocarbon compounds are separated from the gaseous by-products. The remaining gas component is reused as necessary. For example, the unreacted synthesis gas is reused for the FT synthesis reaction, and the carbon dioxide gas is used for reforming the natural gas.

The separation of the carbon dioxide gas from the synthesis gas or gaseous by-products can be performed, for example, by using an absorbent which absorbs the carbon dioxide gas at room temperature, and releases the carbon dioxide gas when it is heated. For example, absorbing carbon dioxide gas included in the synthesis gas and the gaseous by-products by passing those gases through the absorbent at room temperature, and stripping the carbon dioxide gas from the absorbent by heating the absorbent. The absorbent which has released the carbon dioxide gas is reused for separating the carbon dioxide gas from the synthesis gas and the gaseous by-products. Conventionally, in a step of separating the carbon dioxide gas from the synthesis gas and in a step of separating the carbon dioxide gas from the gaseous by-products, circulation systems of the above absorbent are individually provided in the respective steps.

CITATION LIST

Patent Document

[Patent Document 1] Japanese Patent Unexamined Publication No. 2004-323626

SUMMARY OF INVENTION

Technical Problem

In recent years, in the GTL technique, each step including synthesis gas production, FT synthesis reaction, hydrogenation and fractional distillation is desired to be carried out at a low cost. Therefore, even in the above carbon dioxide gas separating step, it is desired to reduce the cost as much as possible.

In view of the above circumstances, the present invention is to provide a method and a system for synthesizing hydrocarbon compounds capable of reducing the cost for absorbing and removing a carbon dioxide gas from a synthesis gas that is a feedstock for the Fischer-Tropsch synthesis reaction and gaseous by-products generated in the Fischer-Tropsch synthesis reaction.

Solution to Problem

The method for synthesizing hydrocarbon compounds according to the present invention is a method for synthesizing liquid hydrocarbon compounds from a synthesis gas by a Fisher-Tropsch synthesis reaction, the method includes: a first absorption step of absorbing a carbon dioxide gas included in gaseous by-products with an absorbent, the gaseous by-products being generated in the Fisher-Tropsch synthesis reaction; and a second absorption step of absorbing a carbon dioxide gas included in the synthesis gas, with the absorbent which has passed through the first absorption step.

In the present invention, since the concentration of the carbon dioxide gas contained in the gaseous by-products is low, a common absorbent is used for the absorption of the carbon dioxide gas contained in the gaseous by-products and the absorption of the carbon dioxide gas included in the synthesis gas.

Therefore, according to the present invention, the cost for absorbing and removing the carbon dioxide gas contained in the synthesis gas and the carbon dioxide gas contained in the gaseous by-products can be reduced, compared to the case using separate absorbents individually for the synthesis gas and the gaseous by-products.

The above method for synthesizing hydrocarbon compounds may further include a merging step of merging the gaseous by-products which have passed through the first absorption step, into the synthesis gas which has passed through the second absorption step before supplying the synthesis gas to the Fisher-Tropsch synthesis reaction.

The gaseous by-products contain a synthesis gas which has not reacted in the Fisher-Tropsch synthesis reaction. According to the present invention, the synthesis gas can be utilized without loss since the synthesis gas which is contained in the gaseous by-products can be reused for the Fisher-Tropsch synthesis reaction.

The above method for synthesizing hydrocarbon compounds may further include a regenerating step of stripping the carbon dioxide gas from the absorbent which has passed through the second absorption step.

In the present invention, the carbon dioxide gas absorbed by the absorbent in the first absorption step and the second absorption step can be stripped from the absorbent at once in the single regenerating step.

Therefore, according to the present invention an apparatus such as a regeneration tower which regenerates the absorbent can be used commonly, and the cost required for synthesizing the liquid hydrocarbon compounds can be reduced, compared to the case using separate absorbents for the synthesis gas and the gaseous by-products, and releasing the carbon dioxide gas individually from the different absorbents.

In the above method for synthesizing hydrocarbon compounds, the absorbent which has passed through the regenerating step may be used in the first absorption step.

In the present invention, stripping the carbon dioxide gas from the absorbent which has passed through first and second absorption steps to regenerate the absorbent, the regenerated absorbent can be reused. Therefore, according to the present invention, the absorbent can be used without loss.

In the above method for synthesizing hydrocarbon compounds, a part of the absorbent which has passed through the regenerating step may be also used in the second absorption step.

In the present invention, a clean absorbent regenerated in the regeneration step can be used as a part of the absorbent in the second absorption step. Accordingly, the carbon dioxide gas contain in the synthesis gas can be absorbed and removed more certainly.

In the above method for synthesizing hydrocarbon compounds, a first supplying position of the absorbent which has passed through the regenerating step may be downstream in a flow of the synthesis gas in the second absorption step with respect to a second supplying position of the absorbent which has passed through the first absorption step.

According to the present invention, the carbon dioxide gas can be absorbed more certainly, since a cleaner absorbent is supplied to a downstream in a flow of the synthesis gas.

In the above method for synthesizing hydrocarbon compounds, the synthesis gas may flow in a direction opposite to the absorbent in the second absorption step.

According to the present invention, the carbon dioxide gas can be more efficiently absorbed, since the synthesis gas flows in the direction opposite to the absorbent in the second absorption step.

The system for synthesizing hydrocarbon compounds according to the present invention is a system for synthesizing liquid hydrocarbon compounds from a synthesis gas by a Fisher-Tropsch synthesis reaction. The system includes: a first absorption tower which allows an absorbent to absorb carbon dioxide gas contained in gaseous by-products generated in the synthesis reaction; and a second absorption tower which allows the absorbent which has passed through the first absorption tower, to absorb carbon dioxide gas contained in the synthesis gas.

In the present invention, common absorbent is used in the first absorption tower and the second absorption tower. Accordingly, an apparatus such as a regeneration tower which regenerates the absorbent can be used commonly, and the cost can be reduced compared to the case where separate absorbents are individually circulated and used in the first and second absorption towers.

The above system for synthesizing hydrocarbon compounds may further include merging section which merges the gaseous by-products discharged from the first absorption tower into the synthesis gas discharged from the second absorption tower.

In the present invention, an unreacted synthesis gas contained in the gaseous by-products from which the carbon dioxide gas has been separated can be reused for the Fisher-Tropsch synthesis reaction. Accordingly, the partial pressure increase of the carbon dioxide gas in the Fisher-Tropsch synthesis reactor is avoided, so that the pressure in the Fisher-Tropsch synthesis reaction can be lowered, and the cost, for example, reactor cost can be reduced.

The above system for synthesizing hydrocarbon compounds may further include a regeneration tower which allows the absorbent which has passed through the second absorption tower to strip the carbon dioxide gas.

In the present invention, the carbon dioxide gas absorbed in the first absorption tower and the second absorption tower can be removed from the absorbent at once in one regeneration tower. Accordingly, the regeneration tower can be used commonly, and the cost, for example, the apparatus cost, can be reduced compared to the case where the carbon dioxide gas is individually removed from different absorbents.

The system for synthesizing hydrocarbon compounds may further include a first supplying section which supplies the absorbent which has passed through the regeneration tower, to the first absorption tower.

According to the present invention, the absorbent from which the carbon dioxide gas has been stripped can be reused, and the absorbent can be used without loss.

The above system for synthesizing hydrocarbon compounds may further include a second supplying section which supplies a part of the absorbent which has passed through the regeneration tower, to the second absorption tower.

In the present invention, the regenerated clean absorbent which has passed through the regeneration tower is supplied to the second absorption tower via the second supplying section, and then the regenerated clean absorbent can be used as a part of the absorbent in the second absorption tower. Accordingly, the carbon dioxide gas contained in the synthesis gas can be absorbed and removed more certainly.

In the above system for synthesizing hydrocarbon compounds, it may be adopted such that the first supplying section includes a first supplying port of the absorbent which is connected to the second absorption tower and through which the absorbent is supplied to the second absorption tower, the second supplying section includes a second supplying port of the absorbent which is connected to the second absorption tower and through which the absorbent is supplied to the second absorption tower, and the second supplying port is positioned at downstream in a flow of the synthesis gas in the second absorption tower with respect to the first supplying port.

According to the present invention, the carbon dioxide gas can be absorbed by the absorbent more certainly, since a cleaner absorbent is supplied to the downstream in the flow of the synthesis gas in the second absorption tower.

In the above system for synthesizing hydrocarbon compounds, the synthesis gas may flow in a direction opposite to the absorbent in the second absorption tower.

In the present invention, the carbon dioxide gas can be more efficiently absorbed, since the synthesis gas flows in the direction opposite to the absorbent in the second absorption tower.

Advantageous Effects of Invention

According to the present invention, there is provided a method and a system for synthesizing hydrocarbon compounds capable of reducing the cost for absorbing and removing carbon a dioxide gas from a synthesis gas that is a feedstock for the Fischer-Tropsch synthesis reaction and gaseous by-products generated in the Fischer-Tropsch synthesis reaction.

DESCRIPTION OF EMBODIMENTS

An embodiment of the present invention will be described below in detail, referring to the accompanying drawings. In the present specification and drawings, duplicate descriptions will be omitted by giving the same reference numbers to components having substantially the same configurations.

Figure 1:
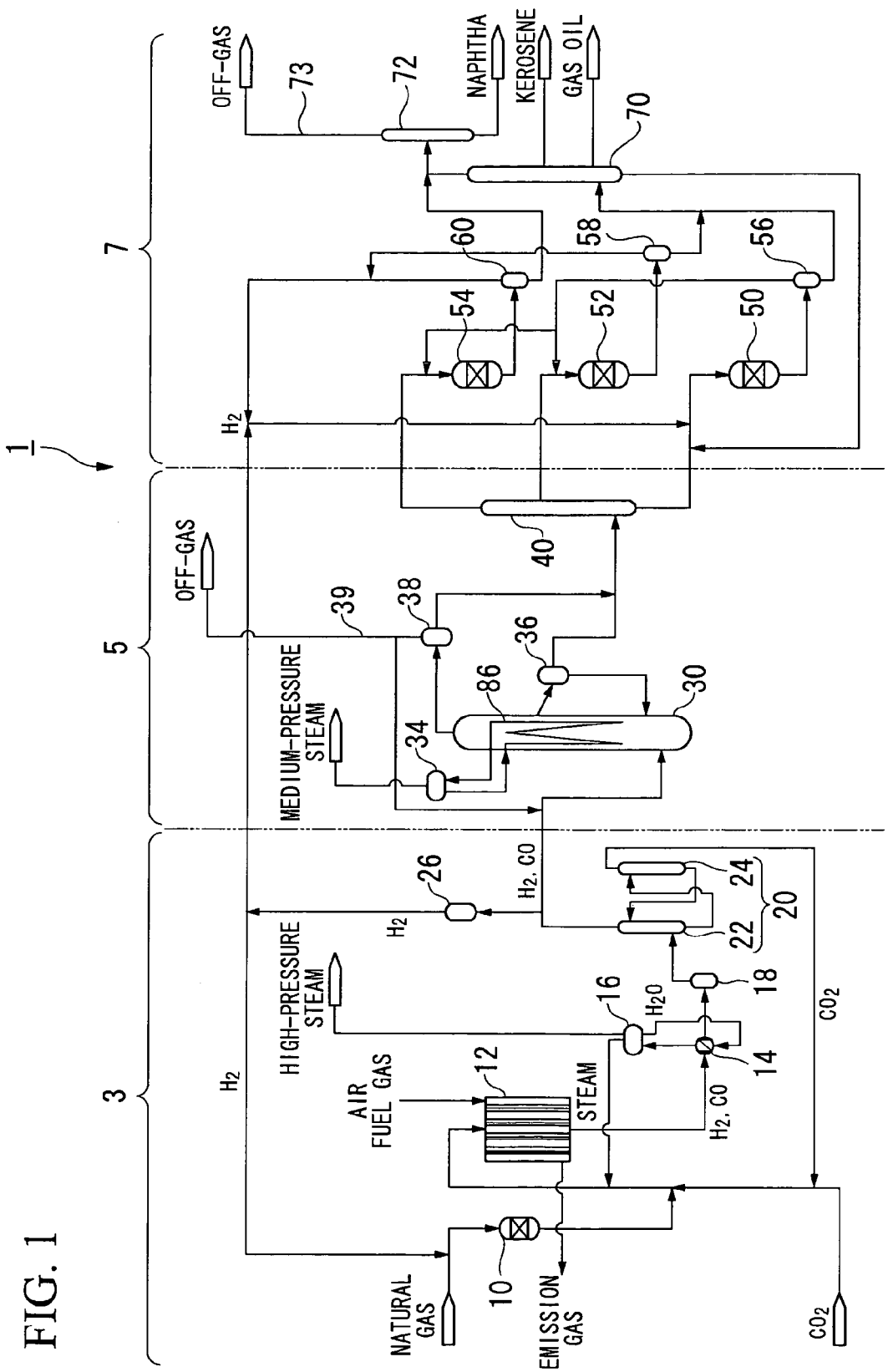
FIG. 1 is an overall schematic diagram showing the configuration of a liquid fuel synthesizing system according to an embodiment of the present invention.

First, with reference to FIG. 1, the overall configuration of a liquid fuel synthesizing system 1 which carries out a GTL (Gas To Liquids) process according to the present embodiment will be described. FIG. 1 is a schematic view showing the overall configuration of the liquid fuel synthesizing system 1 according to the present embodiment.

As shown in FIG. 1, the liquid fuel synthesizing system 1 according to the present embodiment is a plant facility which carries out the GTL process which converts a hydrocarbon feedstock, such as a natural gas, into liquid fuels. The liquid fuel synthesizing system 1 includes a synthesis gas production unit 3, an FT synthesis unit 5, and an upgrading unit 7. The synthesis gas production unit 3 reforms a natural gas, which is a hydrocarbon feedstock, to produce a synthesis gas including a carbon monoxide gas and a hydrogen gas. The FT synthesizing unit 5 synthesizes liquid hydrocarbon compounds from the produced synthesis gas by the FT synthesis reaction. The upgrading unit 7 hydrogenates and fractionates the liquid hydrocarbon compounds synthesized by the FT synthesis reaction to produce liquid fuels and other products (for example, naphtha, kerosene, gas oil, and wax). Hereinafter, components of these respective units will be described.

First, the synthesis gas production unit 3 will be described. The synthesis gas production unit 3 mainly includes, for example, a desulfurization reactor 10, a reformer 12, a waste heat boiler 14, gas-liquid separators 16 and 18, a $CO_2$ removal unit 20, and a hydrogen separator 26. The desulfurization reactor 10 is composed of, for example, a hydrodesulfurizer and removes sulfur components from a natural gas that is a feedstock. The reformer 12 reforms the natural gas supplied from the desulfurization reactor 10 to produce a synthesis gas including a carbon monoxide gas (CO) and a hydrogen gas ($H_2$) as main components. The waste heat boiler 14 recovers waste heat of the synthesis gas produced in the reformer 12 to generate a high-pressure steam. The gas-liquid separator 16 separates the water heated by the heat exchange with the synthesis gas in the waste heat boiler 14 into gas (high-pressure steam) and liquid. The gas-liquid separator 18 removes a condensed component from the synthesis gas cooled down in the waste heat boiler 14, and supplies a gas component to the $CO_2$ removal unit 20. The $CO_2$ removal unit 20 has an absorption tower (second absorption tower) 22 and a regeneration tower 24. In the absorption tower 22, carbon dioxide gas contained in the synthesis gas supplied from the gas-liquid separator 18 is absorbed by an absorbent. In the regeneration tower 24, absorbent which has absorbed the carbon dioxide gas releases the carbon dioxide gas, and the absorbent is regenerated. The hydrogen separator 26 separates a part of the hydrogen gas included in the synthesis gas, from which the carbon dioxide gas has been separated by the $CO_2$ removal unit 20. However, the above $CO_2$ removal unit 20 may not be provided depending on circumstances.

In the reformer 12, for example, by using steam and carbon dioxide gas reforming method described by the chemical reaction formulas (1) and (2), a natural gas is reformed by a carbon dioxide and a steam, and a high temperature synthesis gas which includes a carbon monoxide gas and a hydrogen gas as main components is produced. In addition, the reforming method in this reformer 12 is not limited to the above steam and carbon dioxide gas reforming method. For example, a steam reforming method, a partial oxidation reforming method (PDX) using oxygen, an autothermal reforming method (ATR) that is a combination of the partial oxidation method and the steam reforming method, or a carbon dioxide gas reforming method can also be utilized.

$$CH_4 + H_2O \rightarrow CO + 3H_2 \tag{1}$$

$$CH_4 + CO_2 \rightarrow 2CO + 2H_2 \tag{2}$$

The hydrogen separator 26 is provided on a branch line branching from a main line 28 which connects the $CO_2$ removal unit 20 or gas-liquid separator 18 with the bubble column reactor 30. The hydrogen separator 26 can be composed of, for example, a hydrogen PSA (Pressure Swing Adsorption) device which performs adsorption and desorption of hydrogen by using a pressure difference. The hydrogen PSA device has adsorbents (for example, zeolitic adsorbent, activated carbon, alumina, silica gel) within adsorption towers (not shown) which are arranged in parallel. The hydrogen PSA device can continuously supply a high-purity hydrogen gas (for example, about 99.999%) separated from synthesis gas by sequentially repeating pressurizing, adsorption, desorption (depressurizing), and purging of hydrogen in each adsorption tower.

The hydrogen gas separating method in the hydrogen separator 26 is not limited to the pressure swing adsorption method by the above hydrogen PSA device. For example, a hydrogen storing alloy adsorption method, a membrane separation method, or a combination thereof can be used.

The hydrogen storing alloy method is, for example, a technique for separating hydrogen gas using a hydrogen storing alloy (for example, TiFe, LaNi$_5$, TiFe$_{0.7}$ to TiFe$_{0.9}$, Mn$_{0.3}$ to Mn$_{0.1}$, TiMn$_{1.5}$) having a property which adsorbs or releases a hydrogen by being cooled or heated respectively. In the hydrogen storing alloy method, for example, within adsorption towers which contains a hydrogen storing alloy, absorption of a hydrogen by cooling the hydrogen storing alloy and releasing of a hydrogen by heating the hydrogen storing alloy are alternately repeated. In this way, hydrogen gas in the synthesis gas can be separated and recovered.

The membrane separation method is a method using a membrane made of a polymer material, such as aromatic polyimide to separate a hydrogen gas, which has superior membrane permeability, from a mixed gas. Since the membrane separation method does not require a phase change of the objective materials for separation, less energy is required for the operation, and the operation cost is small. Additionally, since the structure of a membrane separation device is simple and compact, low facility cost is required and the required facility area is also small. Moreover, since there is no driving device in a separation membrane, and a stable operating range is wide, there is an advantage that maintenance is easy.

Next, the FT synthesis unit 5 will be described. The FT synthesis unit 5 mainly includes, for example, the bubble column reactor 30, a gas-liquid separator 34, a separator 36, a gas-liquid separator 38, and a first fractionator 40. The bubble column reactor 30 synthesizes liquid hydrocarbon compounds by the FT synthesis reaction from the synthesis gas produced in the above synthesis gas production unit 3, more specifically, from a carbon monoxide gas and a hydrogen gas. The gas-liquid separator 34 separates the water, which is heated while passing through the heat transfer tube 86 provided within the bubble column reactor 30, into a steam (medium-pressure steam) and liquid. The separator 36 is connected to a middle part of the bubble column reactor 30 to separate a catalyst and liquid hydrocarbon compounds. The gas-liquid separator 38 is connected to the top of the bubble column reactor 30 to cool down an unreacted synthesis gas and gaseous hydrocarbon compounds (gaseous by-products). The first fractionator 40 fractionally distills the liquid hydrocarbon compounds, which are supplied via the separator 36 and the gas-liquid separator 38 from the bubble column reactor 30, into respective fractions.

The bubble column reactor 30, which is an example of a reactor which synthesizes liquid hydrocarbon compounds from the synthesis gas, functions as an FT synthesis reactor which synthesizes liquid hydrocarbon compounds from the synthesis gas by the FT synthesis reaction. The bubble column reactor 30 is composed of, for example, a bubble column slurry bed type reactor in which slurry consisting of a catalyst and a medium oil is contained inside a column type vessel. This bubble column reactor 30 synthesizes liquid hydrocarbon compounds from the synthesis gas by the FT synthesis reaction. In detail, the synthesis gas supplied to the bubble column reactor 30 flows through the slurry consisting of a catalyst and medium oil. And in a suspended state, a hydrogen gas and a carbon monoxide gas included in the synthesis gas react with each other to synthesize hydrocarbon compounds, as shown in the following chemical reaction formula (3).

$$2n\mathrm{H}_2 + n\mathrm{CO} \rightarrow -(\mathrm{CH}_2)_n- + n\mathrm{H}_2\mathrm{O} \qquad (3)$$

Since this FT synthesis reaction is an exothermic reaction, the bubble column reactor 30 is a heat exchanger type reactor within which the heat transfer tube 86 is provided. The bubble column reactor 30 is supplied with, for example, water (BFW: Boiler Feed Water) as a coolant, so that the reaction heat of the above FT synthesis reaction can be recovered as a medium-pressure steam by the heat exchange between the slurry and the water.

Next, the upgrading unit 7 will be described. The upgrading unit 7 includes, for example, a wax fraction hydrocracking reactor 50, a middle distillate hydrotreating reactor 52, a naphtha fraction hydrotreating reactor 54, gas-liquid separators 56, 58, and 60, a second fractionator 70, and a naphtha stabilizer 72. The wax fraction hydrocracking reactor 50 is connected to the bottom of the first fractionator 40. The middle distillate hydrotreating reactor 52 is connected to a middle part of the first fractionator 40. The naphtha fraction hydrotreating reactor 54 is connected to the top of the first fractionator 40. The gas-liquid separators 56, 58 and 60 are provided so as to correspond to the hydrogenation reactors 50, 52 and 54, respectively. The second fractionator 70 fractionally distills the liquid hydrocarbon compounds supplied from the gas-liquid separators 56 and 58. The naphtha stabilizer 72 rectifies liquid hydrocarbon compounds of a naphtha fraction which are supplied from the gas-liquid separator 60 and fractionally distilled in the second fractionator 70. As the result, the naphtha stabilizer 72 discharges butane and components lighter than butane as a off-gas, and recovers components having a carbon number of five or more as a naphtha product.

Next, a process for synthesizing liquid fuels from a natural gas (GTL process) by the liquid fuel synthesizing system 1 configured as above will be described.

A natural gas (the main component of which is $CH_4$) as a hydrocarbon feedstock is supplied to the liquid fuel synthesizing system 1 from an external natural gas supply source (not shown), such as a natural gas field or a natural gas plant. The above synthesis gas production unit 3 reforms the natural gas to produce a synthesis gas (mixed gas including a carbon monoxide gas and a hydrogen gas as main components).

Specifically, at first, the natural gas is introduced into the desulfurization reactor 10 along with the hydrogen gas separated by the hydrogen separator 26. In the desulfurization reactor 10, sulfur components included in the natural gas are converted into a hydrogen sulfide by the introduced hydrogen gas and the hydrodesulfurization catalyst. Further, in the desulfurization reactor 10, the generated hydrogen sulfide is absorbed by a desulfurizing agent, for example, ZnO. By desulfurizing the natural gas in advance in this way, reduction in activity of catalysts used in the reformer 12 and the bubble column reactor 30 due to sulfur can be prevented.

The natural gas (may also include a carbon dioxide) desulfurized in this way is supplied to the reformer 12 after the carbon dioxide ($CO_2$) gas supplied from a carbon dioxide supply source (not shown) and the steam generated in the waste heat boiler 14 are mixed together. In the reformer 12, the natural gas is reformed by the carbon dioxide and the steam, and a high-temperature synthesis gas including a carbon monoxide gas and a hydrogen gas as main components is produced, for example, by the above steam and carbon dioxide gas reforming method. At this time, a fuel gas and an air for a burner installed in the reformer 12 are supplied to the reformer 12. And by the combustion heat of the fuel gas in the burner, reaction heat required for the above steam and carbon dioxide gas reforming reaction that is an endothermic reaction is provided.

The high-temperature synthesis gas (for example, 900° C., 2.0 MPaG) produced in the reformer 12 in this way is supplied to the waste heat boiler 14, and is cooled down by the heat exchange with the water which circulates through the waste heat boiler 14 (for example, 400° C.). And the waste heat of the synthesis gas is recovered by the water. At this time, the water heated by the synthesis gas in the waste heat boiler 14 is supplied to the gas-liquid separator 16. In the gas-liquid separator 16, the water heated by the synthesis gas is separated into a high pressure steam (for example, 3.4 to 10.0 MPaG) and water. The separated high pressure steam is supplied to the reformer 12 or other external devices, and separated water is returned to the waste heat boiler 14.

Meanwhile, the synthesis gas cooled down in the waste heat boiler 14 is supplied to the absorption tower 22 of the $CO_2$ removal unit 20, or the bubble column reactor 30, after a condensed liquid fraction is separated and removed from the synthesis gas in the gas-liquid separator 18. In the absorption tower 22, a carbon dioxide gas contained in the synthesis gas is absorbed by the absorbent which is contained in the absorption tower 22, and the carbon dioxide gas is removed from the synthesis gas. The absorbent which has absorbed the carbon dioxide gas within this absorption tower 22 is discharged from the absorption tower and introduced into the regeneration tower 24. The absorbent which is introduced into the regeneration tower 24 is heated with, for example, a steam and subjected to stripping treatment to release the carbon dioxide gas. The released carbon dioxide gas is discharged from the regeneration tower 24 and introduced into the reformer 12, and is reused for the above reforming reaction.

The synthesis gas produced in the synthesis gas production unit 3 in this way is supplied to the bubble column reactor 30 of the above FT synthesis unit 5. At this time, the composition ratio of the synthesis gas supplied to the bubble column reactor 30 is adjusted to a composition ratio suitable for the FT synthesis reaction (for example, $H_2:CO=2:1$ (molar ratio)). In addition, the synthesis gas supplied to the bubble column reactor 30 is pressurized to a pressure suitable for the FT synthesis reaction (for example, about 3.6 MPaG) by a compressor (not shown) provided in a line which connects the $CO_2$ removal unit 20 with the bubble column reactor 30.

Additionally, a part of the synthesis gas, the carbon dioxide gas of which has been separated by the above $CO_2$ removal unit 20, is also supplied to the hydrogen separator 26. In the hydrogen separator 26, the hydrogen gas contained in the synthesis gas is separated by the adsorption and desorption utilizing a pressure difference (hydrogen PSA) as described above. The separated hydrogen is continuously supplied from, for example, a gas holder (not shown) via a compressor (not shown) to various hydrogen-utilizing reaction devices (for example, the desulfurization reactor 10, the wax fraction hydrocracking reactor 50, the middle distillate hydrotreating reactor 52, the naphtha fraction hydrotreating reactor 54) which perform predetermined reactions by utilizing hydrogen within the liquid fuel synthesizing system 1.

Next, the above FT synthesis unit 5 synthesizes liquid hydrocarbon compounds by the FT synthesis reaction from the synthesis gas produced by the above synthesis gas production unit 3.

Specifically, the synthesis gas, from which the carbon dioxide gas has been separated in the above $CO_2$ removal unit 20, is introduced into the bubble column reactor 30, and flows through the slurry including the catalyst contained in the bubble column reactor 30. At this time, within the bubble column reactor 30, the carbon monoxide and hydrogen gas which are included in the synthesis gas react with each other by the aforementioned FT synthesis reaction, and hydrocarbon compounds are produced. Moreover, while the FT synthesis reaction, the reaction heat of the FT synthesis reaction is recovered by the water flowing through the heat transfer tube 86 of the bubble column reactor 30, and the water heated by the reaction heat is vaporized into a steam. The steam is supplied to the gas-liquid separator 34 and separated into condensed water and a gas fraction, the water is returned to the heat transfer tube 86, and the gas fraction is supplied to an external device as a medium-pressure steam (for example, 1.0 to 2.5 MPaG).

The liquid hydrocarbon compounds synthesized in the bubble column reactor 30 in this way are discharged from the middle part of the bubble column reactor 30 as a slurry including catalyst particles, and are introduced into the separator 36. In the separator 36, the introduced slurry is separated into catalysts (solid particle) and a liquid component including a liquid hydrocarbon compounds. A part of the separated catalyst is returned to the bubble column reactor 30, and the liquid component is introduced into the first fractionator 40. From the top of the bubble column reactor 30, gaseous by-products, which include an unreacted synthesis gas in the FT synthesis reaction and gaseous hydrocarbon compounds generated in the FT synthesis reaction, are discharged. The gaseous by-products discharged from the bubble column reactor 30 are introduced into the gas-liquid separator 38. In the gas-liquid separator 38, the gaseous by-products are cooled down, and are separated into condensed liquid hydrocarbon compounds and gas component. Separated liquid hydrocarbon compounds are discharged from the gas-liquid separator 38, and are introduced into the first fractionator 40. A part of the separated gas component discharged from the gas-liquid separator 38 is reintroduced into the bubble column reactor 30, and the unreacted synthesis gases (CO and $H_2$) contained in this gas component are reused for the FT synthesis reaction. Further, the off-gas discharged from the gas-liquid separator 38 including gaseous hydrocarbon compounds, which have a small carbon number ($C_4$ or less) that is other than target products as a main component, is used as a fuel gas, or fuels equivalent to LPG (Liquefied Petroleum Gas) is recovered.

In the first fractionator 40, the liquid hydrocarbon compounds (with variety of carbon number), which are supplied via the separator 36 and the gas-liquid separator 38 from the bubble column reactor 30 as described above, are fractionally distilled into a naphtha fraction (the boiling point of which is lower than about 150° C.), a middle distillate (the boiling point of which is about 150 to 350° C.), and a wax fraction (the boiling point of which exceeds about 350° C.). The liquid hydrocarbon compounds of the wax fraction (mainly $C_{21}$ or more) discharged from the bottom of the first fractionator 40 are introduced into the wax fraction hydrocracking reactor 50. The liquid hydrocarbon compounds of the middle distillate equivalent to kerosene and gas oil (mainly $C_{11}$ to $C_{20}$) discharged from the middle part of the first fractionator 40 are introduced into the middle distillate hydrotreating reactor 52. The liquid hydrocarbon compounds of the naphtha fraction (mainly $C_5$ to $C_{10}$) discharged from the top of the first fractionator 40 are introduced into the naphtha fraction hydrotreating reactor 54.

The wax fraction hydrocracking reactor 50 hydrocracks the liquid hydrocarbon compounds of the wax fraction with a large carbon number (approximately $C_{21}$ or more), which are discharged from the bottom of the first fractionator 40, by using the hydrogen gas supplied from the above hydrogen separator 26, to reduce the carbon number to $C_{20}$ or less. In this hydrocracking reaction, C—C bonds of hydrocarbon compounds with a large carbon number are cleaved by the action of catalysts and heat. As the result, the hydrocarbon compounds with a large carbon number are converted into hydrocarbon compounds with a small carbon number. Additionally, in the wax fraction hydrocracking reactor 50, the reaction which hydroisomerizes straight chain saturated hydrocarbon compounds (normal paraffins) to produced branched saturated hydrocarbon compounds (isoparaffins) also proceeds simultaneously with the hydrocracking reaction. This improves the low-temperature fluidity of a wax fraction hydrocracking product which is required as a base stock of fuel oil. Moreover, in the wax fraction hydrocracking reactor 50, a hydrodeoxygenation reaction of oxygen-containing compounds, such as alcohols, and a hydrogenation reaction of olefins, both of which are contained in a wax fraction that is a feedstock, also proceed. The hydrocracked products including the liquid hydrocarbon compounds discharged from the wax fraction hydrocracking reactor 50 are introduced into gas-liquid separator 56, and separated into gas and liquid. The separated liquid hydrocarbon compounds are introduced in to the second fractionator 70, and the separated gas component (including a hydrogen gas) is introduced into the middle distillate hydrotreating reactor 52 and the naphtha fraction hydrotreating reactor 54.

In the middle distillate hydrotreating reactor 52, liquid hydrocarbon compounds of the middle distillate equivalent to kerosene and gas oil having a middle carbon number (approximately $C_{11}$ to $C_{20}$), which are discharged from the middle part of the first fractionator 40, are hydrotreated. In the middle distillate hydrotreating reactor 52, a hydrogen gas supplied from the hydrogen separator 26 via the wax fraction hydrocracking reactor 50 is used for the hydrotreating. In this hydrotreating reaction, the olefins contained in the above liquid hydrocarbon compounds is hydrogenated to produce saturated hydrocarbon compounds, and the oxygen-containing compounds, such as alcohols contained in the above liquid hydrocarbon compounds are hydrodeoxygenated and converted into saturated hydrocarbon compounds and water. Moreover, in this hydrotreating reaction, a hydroisomerization reaction which isomerizes straight chain saturated hydrocarbon compounds (normal paraffins) to convert the saturated hydrocarbon compounds into branched saturated hydrocarbon compounds (isoparaffins) proceeds, and the low-temperature fluidity of the produced oil which is required as a fuel oil is improved. A product including the hydrotreated liquid hydrocarbon compounds is separated into gas and liquid in the gas-liquid separator 58. The separated liquid hydrocarbon compounds are introduced into the second fractionator 70, and the separated gas fraction (including a hydrogen gas) is reused for the above hydrogenation reaction.

In the naphtha fraction hydrotreating reactor 54, liquid hydrocarbon compounds of the naphtha fraction with a low carbon number (approximately $C_{10}$ or less), which are discharged from the top of the first fractionator 40, are hydrotreated. In the naphtha fraction hydrotreating reactor 54, the hydrogen gas supplied from the hydrogen separator 26 via the wax fraction hydrocracking reactor 50 is used for the hydrotreating. As a result, a product including the hydrotreated liquid hydrocarbon compounds is separated into gas and liquid in the gas-liquid separator 60. The separated liquid hydrocarbon compounds are introduced into the naphtha stabilizer 72, and the separated gas fraction (including hydrogen gas) is reused for the above hydrogenation reaction. In this naphtha fraction hydrotreating, hydrogenation of olefins, and hydrodeoxygenation of oxygen-containing compounds such as alcohols mainly proceed.

In the second fractionator 70, the liquid hydrocarbon compounds, which are supplied from the wax fraction hydrocracking reactor 50 and the middle distillate hydrotreating reactor 52 as described above, are fractionally distilled into hydrocarbon compounds of $C_{10}$ or less (the boiling point of which is lower than about 150° C.), a kerosene fraction (the boiling point of which is about 150 to 250° C.), a gas oil (the boiling point of which is about 250 to 350° C.), and an uncracked wax fraction (the boiling point of which exceeds 350° C.) from the wax fraction hydrocracking reactor 50. The uncracked wax fraction is obtained from the bottom of the second fractionator 70, and this is recycled to the upstream of the wax fraction hydrocracking reactor 50. Kerosene and gas oil are discharged from the middle part of the second fractionator 70. Meanwhile, gaseous hydrocarbon compounds of $C_{10}$ or less is discharged from the top of the second fractionator 70, and is introduced into the naphtha stabilizer 72.

Moreover, in the naphtha stabilizer 72, the hydrocarbon compounds of $C_{10}$ or less, which have been supplied from the above naphtha fraction hydrotreating reactor 54 and fractionally distilled in the second fractionator 70, are distilled, and naphtha ($C_5$ to $C_{10}$) is obtained as a product. Accordingly, high-purity naphtha is discharged from the bottom of the naphtha stabilizer 72. Meanwhile, the off-gas including hydrocarbon compounds with a predetermined carbon number or less ($C_4$ or less), which is other than the product, is discharged from the top of the naphtha stabilizer 72. This off-gas is used as a fuel gas, or a fuel equivalent to LPG is recovered.

The process (GTL process) of the liquid fuel synthesizing system 1 has been described hitherto. By this GTL process, a natural gas can be easily and economically converted into clean liquid fuels, such as high-purity naphtha ($C_5$ to $C_{10}$), kerosene ($C_{11}$ to $C_{15}$), and gas oil ($C_{16}$ to $C_{20}$).

Figure 2:
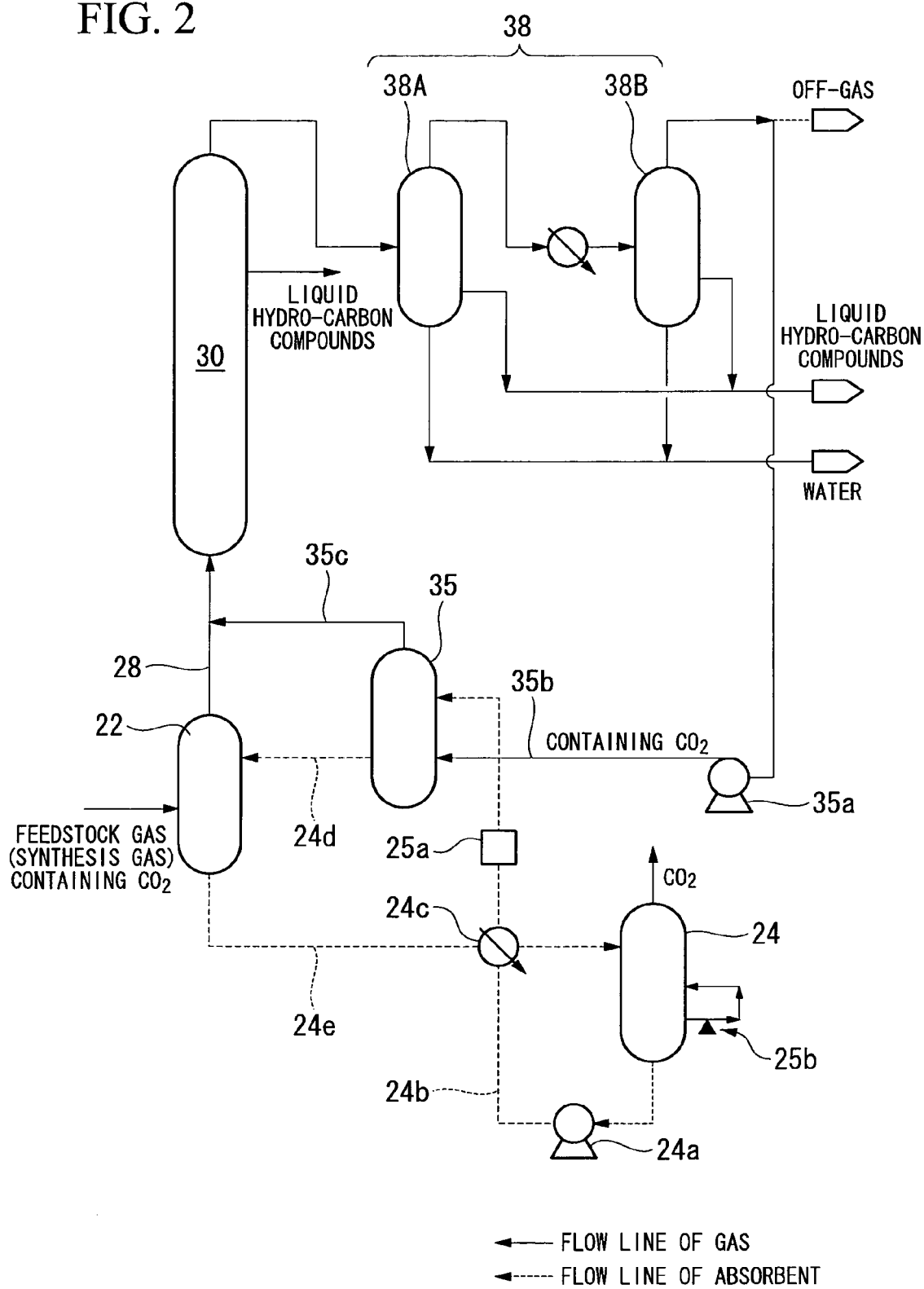
FIG. 2 is a partial schematic diagram showing the configuration of the hydrocarbon compounds synthesizing system.

Next, a configuration of a part of the liquid fuel synthesis system 1, which removes a carbon dioxide gas from a synthesis gas and gaseous by-products, will be described with reference to FIG. 2. In the present embodiment, a configuration using an absorbent to remove the carbon dioxide gas will be described as an example. The absorbent used in the present embodiment has a feature of absorbing a carbon dioxide gas at room temperature, and releasing the absorbed carbon dioxide gas when it is heated. In FIG. 2, lines shown in a solid-line arrow are those of the gases, and lines shown in a broken-line arrow are those of the absorbent. In addition, the above absorbent includes, for example, aqueous solutions of amine compounds given as the following general formulas (4) to (6).

$$R_1R_2N(CH_2)_nOH \tag{4}$$

$$R_1N((CH_2)_nOH)_2 \tag{5}$$

$$N((CH_2)_nOH)_3 \tag{6}$$

Here, in the formulas (4) to (6), $R_1$ is a hydrogen atom or an alkyl group of $C_1$ to $C_{10}$, and $R_2$ is a hydrogen atom or an alkyl group of $C_1$ to $C_4$. Additionally, n=1 to 5. Moreover, hydroxyalkyl groups in Formula (5) and Formula (6) shall include a case where the carbon numbers of alkylene groups are different from each other.

Such amine compounds include, for example, alkanolamines, such as monoethanolamine, diethanolamine, triethanolamine, 2-methylamino ethanol, 2-ethylamino ethanol, 2-propylamino ethanol, n-butylamino ethanol, 2-(isopropyl amino)ethanol, 3-ethylamino propanol, and dipropanol amine. The concentration of the amine compounds in an aqueous solution is set to 20 to 80 mass %, and is more preferably set to 30 to 50 mass %.

Additionally, absorbents other than the aqueous solution of the amine compounds may be used.

First, the flow lines of the gaseous by-products separated by the gas-liquid separator 38 will be described. The gas-liquid separator 38 is connected to a main line 28 via a gaseous by-product line 35b, a first absorption tower 35, and a merging line 35c. The gaseous by-product line 35b is provided with, for example, a compressor 35a. The gaseous by-product line 35b is connected to the first absorption tower 35. In the first absorption tower 35, a carbon dioxide gas, which is contained in the gaseous by-products supplied through the gaseous by-product line 35b, is absorbed by the above absorbent (first absorption step). The merging line 35c connects the top of the first absorption tower 35 and the main line 28. The merging line 35c is a merging section which merges the gaseous by-products, from which the carbon dioxide gas is removed while passing through the first absorption tower 35, into the synthesis gas flowing in the main line 28.

Next, the flow lines of the absorbent will be described. The absorbent is circulated between the regeneration tower 24 (refer to FIG. 1), the first absorption tower 35, and the second absorption tower 22. The regeneration tower 24 is connected to the upper part of the first absorption tower 35 via first supplying line (first supplying section) 24b. The supplying line 24b is provided with a pump 24a, a heat exchanger 24c, and a cooler 25a. The bottom of the regeneration tower 24 is provided with a circulation path of the absorbent. A heating part 25b which heats the absorbent is provided on the circulation lines.

The first absorption tower 35 is connected to an upper part of the second absorption tower 22 via second supplying line (second supplying section) 24d. One end of the second supplying line 24d is connected to a lower part of the first absorption tower 35, and the other end of the second supplying line 24d is connected to an upper part of the second absorption tower 22. The second absorption tower 22 is connected to the regeneration tower 24 via third supplying line 24e. One end of the third supplying line 24e is connected to a lower part of the second absorption tower 22 and the other end of the third supplying line 24e is connected to the regeneration tower 24. The third supplying line 24e is passing through inside of the above heat exchanger 24c.

Next, a step of absorbing carbon dioxide gas will be described while describing the flow lines of the gaseous by-products and the flow lines of the absorbent, and the flow lines of the synthesis gas.

The gaseous by-products separated by the gas-liquid separator 38 are supplied to the bottom of the first absorption tower 35 via the gaseous by-product line 35b. The gaseous by-products supplied to the first absorption tower 35 move within the first absorption tower 35 from its lower part to its upper part. Meanwhile, the absorbent is supplied to the upper part of the first absorption tower 35 via the supplying line 24b from the regeneration tower 24. The absorbent is cooled down in the cooler 25a while passing through the supplying line 24b. The absorbent supplied to the upper part of the first absorption tower 35 moves within the first absorption tower 35 from its upper part to its lower part.

In the first absorption tower 35, the carbon dioxide gas in the gaseous by-products which move within the first absorption tower 35 from its lower part to its upper part is absorbed by the absorbent which moves within the first absorption tower 35 from its upper part to its lower part (first absorption step). As such, in the first absorption tower 35, a flow direction of the absorbent and a flow direction of the gaseous by-products are opposite, that is a counter flow, while absorbing the carbon dioxide gas in the gaseous by-products by the absorbent.

The gaseous by-products, from which the carbon dioxide gas has been absorbed and removed, are discharged from the first absorption tower 35 through the=merging line 35c which is connected to the first absorption tower 35. Meanwhile, the absorbent which has absorbed the carbon dioxide gas is discharged from the first absorption tower 35 through the second supplying line 24d which is connected to the lower part of the first absorption tower 35.

The volume content of the carbon dioxide gas in the gaseous by-products is, for example, about 0.5% with respect to the whole gaseous by-products, which is a relatively low concentration. For this reason, the absorbent which has absorbed the carbon dioxide gas in the gaseous by-products still has sufficient remained absorption capacity of the carbon dioxide gas. The absorbent which has the sufficient absorption capacity in this way is discharged from the first absorption tower 35.

The absorbent which is discharged from the first absorption tower 35 is introduced into the upper part of the second absorption tower 22 via the second supplying line 24d. The absorbent introduced into the upper part of the second absorption tower 22 moves within the second absorption tower 22 from its upper part to its lower part. Meanwhile, the synthesis gas discharged from the gas-liquid separator 18 (refer to FIG. 1) that is a feedstock for the FT synthesis reaction step is introduced into the lower part of the second absorption tower 22. The synthesis gas introduced into the second absorption tower 22 moves within the second absorption tower 22 from its lower part to its upper part.

In the second absorption tower 22, the carbon dioxide gas in the synthesis gas which moves within the second absorption tower 22 from its lower part to its upper part is absorbed by the absorbent which moves within the second absorption tower 22 from its upper part to its lower part (second absorption step). As such, in the second absorption tower 22, a flow direction of the absorbent and a flow direction of the synthesis gas are opposite, that is a counter flow, while absorbing the carbon dioxide gas in the synthesis gas by the absorbent.

The absorbent used in the second absorption tower 22 is an absorbent which has absorbed the carbon dioxide gas in the gaseous by-products in the first absorption tower 35. That is, a common absorbent is used in the first absorption tower 35 and the second absorption tower 22. As mentioned above, the absorbent has sufficient carbon dioxide gas absorption capacity even after the absorbent has absorbed the carbon dioxide gas in the gaseous by-products. The volume content of the carbon dioxide gas in the synthesis gas is about 5.8% of the whole synthesis gas, which is a relatively high concentration. However, the carbon dioxide gas absorption capacity of the absorbent supplied from the first absorption tower 35 is still sufficient. Therefore, in the second absorption tower 22, the high-concentration carbon dioxide gas in this synthesis gas can be sufficiently absorbed by the absorbent.

The synthesis gas, from which the carbon dioxide gas has been absorbed and removed, is discharged from the second absorption tower 22 to the main line 28. In the main line 28, the gaseous by-products discharged from the first absorption tower 35 merge into the synthesis gas flowing in the main line 28 through the merging line 35c which is connected to the main line 28 (merging step). The merged gaseous by-products and the synthesis gas are introduced into the bubble column reactor 30 through the main line 28. The synthesis gas and an unreacted synthesis gas component contained in the gaseous by-products are used for the FT synthesis reaction in the bubble column reactor 30.

Meanwhile, the absorbent which has absorbed the carbon dioxide gas is discharged from the lower part of the second absorption tower 22 to the third supplying line 24e. The absorbent discharged from the second absorption tower 22 is introduced into the regeneration tower 24 through the third supplying line 24e. In the regeneration tower 24, the absorbent is heated by the heating part 25b, the carbon dioxide gas is removed from the absorbent, and the absorbent is regenerated (regenerating step). The absorbent which has released the carbon dioxide gas and been regenerated is again supplied to the first absorption tower 35 through the supplying line 24b. In the first absorption tower 35, the absorbent which is regenerated by the regenerating step is used, and the carbon dioxide gas in the gaseous by-products is absorbed by the regenerated absorbent (the first absorption step). Thereafter, the carbon dioxide gas contained in the gaseous by-products and the synthesis gas is absorbed by circulating the absorbent as above.

In the method for synthesizing liquid hydrocarbon compounds using the liquid fuel synthesizing system 1 of the present embodiment, focusing on the fact that the concentration of the carbon dioxide gas contained in the gaseous by-products is low, the method for synthesizing hydrocarbon compounds includes the first absorption step of absorbing the carbon dioxide gas contained in the gaseous by-products by the absorbent, and the second absorption step of absorbing the carbon dioxide gas contained in the synthesis gas by the absorbent used in the first absorption step. Thus, the common absorbent can be used for the absorption of the carbon dioxide gas contained in the gaseous by-products and the absorption of the carbon dioxide gas included in the synthesis gas. Accordingly, the cost can be reduced compared to the case where absorbents are individually circulated and used for a step of absorbing the carbon dioxide gas contained in the gaseous by-products, and a step of absorbing the carbon dioxide gas contained in the synthesis gas.

Additionally, according to the present embodiment, the gaseous by-products discharged from the first absorption tower 35 are merged into the synthesis gas discharged from the second absorption tower 22. As the result, unreacted synthesis gas contained in the gaseous by-products, from which the carbon dioxide gas has been absorbed and removed, can be reused for the FT synthesis reaction. Accordingly, the synthesis gas can be utilized without loss. Additionally, the method further includes a regenerating step of heating the absorbent after the second absorption step, stripping the carbon dioxide gas from the absorbent, and regenerating the absorbent. As the result, the carbon dioxide gas absorbed by the absorbent in the first absorption step and the second absorption step can be stripped from the absorbent at once in a single regenerating step. Accordingly, compared to the case where absorbents which have absorbed the carbon dioxide gas in respective absorption steps are individually heated and the carbon dioxide gas are stripped, for example, the regeneration tower 24 can be shared, and the apparatus cost can be reduced.

The technical scope of the present invention is not limited to the above embodiment, but various modifications may be made without departing from the gist of the present invention.

For example, although the configuration in which the absorbent discharged from the regeneration tower 24 is introduced into only the first absorption tower 35 has been described as an example in the above embodiment, the present invention is not limited thereto. For example, as shown in FIG. 3, a configuration in which a part of the absorbent discharged from the regeneration tower 24 is introduced into the second absorption tower 22 may be adopted.

Figure 3:
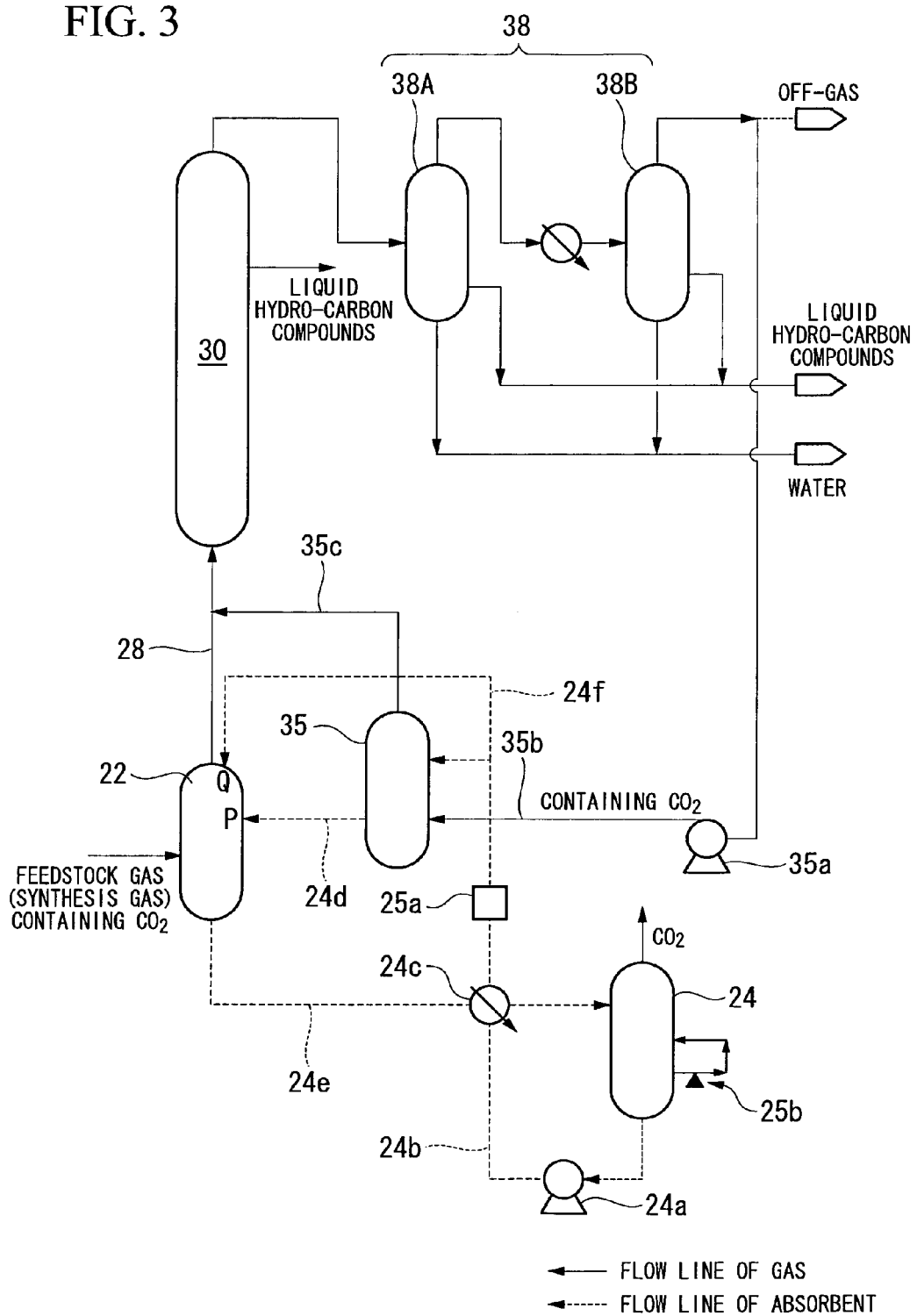
FIG. 3 is a partial schematic diagram showing another configuration of the hydrocarbon compounds synthesizing system according to the present invention.

In a configuration shown in FIG. 3, fourth supplying line 24f branches from the supplying line 24b, in the flow line of the absorbent. The end of the fourth supplying line 24f (second supplying port) Q is connected to the upper part of the second absorption tower 22. The end of the fourth supplying line 24f Q is arranged at a higher position of the second absorption tower 22 than the end of the second supplying line 24d (first supplying port) P which is connected to the second absorption tower. That is, the end of the fourth supplying line 24f Q, which supplies the absorbent passed through the regeneration tower 24, is located at downstream in a flow direction of the synthesis gas in the second absorption tower than the end of the second supplying line P, which supplies the absorbent passed through the first absorption tower 35. For this reason, a clean absorbent will be supplied to further downstream in the flow direction of the synthesis gas.

By adopting such a configuration, a part of the absorbent which has released the carbon dioxide gas and been regenerated can be used in the second absorption step. Thus, a clean absorbent can also be used in the second absorption step. Additionally, a cleaner absorbent is introduced into the downstream in the flow direction of the synthesis gas. Therefore, the carbon dioxide gas which is contained in the synthesis gas can be certainly absorbed. Additionally, the flow of the absorbent and the flow of the synthesis gas are in a counter flow. Thus, the carbon dioxide gas contained in the synthesis gas can be more efficiently absorbed by the absorbent.

Industrial Applicability

According to the method and the system of the present invention, the cost for absorbing and removing a carbon dioxide gas from a synthesis gas that is a feedstock of the Fischer-Tropsch synthesis reaction and gaseous by-products generated in the Fischer-Tropsch synthesis reaction can be reduced

REFERENCE SIGNS LIST

30: BUBBLE COLUMN REACTOR
22: SECOND ABSORPTION TOWER
24: REGENERATION TOWER
24b: SUPPLYING LINE
24d: SECOND SUPPLYING LINE
35: FIRST ABSORPTION TOWER
35c: MERGING LINE

The invention claimed is:

1. A method for synthesizing liquid hydrocarbon compounds comprising:
   a synthesis step of synthesizing liquid hydrocarbon compounds from a synthesis gas containing carbon monoxide gas and hydrogen gas by a Fisher-Tropsch synthesis reaction in a reactor;
   a discharge step of discharging gaseous by-products formed by the Fisher-Tropsch synthesis reaction from the reactor;
   a first absorption step of absorbing carbon dioxide gas contained in the gaseous by-products discharged from the reactor with a first absorbent; and
   a second absorption step of absorbing carbon dioxide gas contained in the synthesis gas to be supplied to the reactor, with a second absorbent; and
   a supply step of supplying the first absorbent which has passed through the first absorption step to the second absorption step as the second absorbent.

2. The method for synthesizing liquid hydrocarbon compounds according to claim 1, further comprising a merging step of merging the gaseous by-products from which the carbon dioxide gas has been removed by the first absorbent into the synthesis gas from which the carbon dioxide gas has been removed by the second absorbent, and which is to be supplied to the reactor.

3. The method for synthesizing liquid hydrocarbon compounds according to claim 1, further comprising a regenerating step of stripping the carbon dioxide gas from the second absorbent which has passed through the second absorption step to regenerate the second absorbent.

4. The method for synthesizing liquid hydrocarbon compounds according to claim 3,
   wherein the absorbent which has passed through the regenerating step is used in the first absorption step as the first absorbent.

5. The method for synthesizing liquid hydrocarbon compounds according to claim 3, wherein a part of the absorbent which has passed through the regenerating step is also used in the second absorption step as the second absorbent.

6. The method for synthesizing liquid hydrocarbon compounds according to claim 5,
wherein the first absorbent which has passed through the first absorption step is supplied to the synthesis gas in the second absorption step, and thereafter the absorbent which has passed through the regenerating step is supplied to the synthesis gas in the second absorption step.

7. The method for synthesizing liquid hydrocarbon compounds according to claim 1,
wherein the synthesis gas flows in a direction opposite to the second absorbent in the second absorption step.

8. The method for synthesizing liquid hydrocarbon compounds according to claim 1, wherein the absorbent includes aqueous solutions of amine compounds represented by the following formulas (1) to (3), $$R_1R_2N(CH_2)_nOH \qquad (1)$$

$$R_1N((CH_2)_nOH)_2 \qquad (2)$$

$$N((CH_2)_nOH)_3 \qquad (3)$$

wherein $R_1$ is a hydrogen atom or an alkyl group of $C_1$ to $C_{10}$, $R_2$ is a hydrogen atom or an alkyl group of $C_1$ to $C_4$, and n=1 to 5.

* * * * *

UNITED STATES PATENT AND TRADEMARK OFFICE
CERTIFICATE OF CORRECTION

PATENT NO. : 8,877,821 B2
APPLICATION NO. : 13/138675
DATED : November 4, 2014
INVENTOR(S) : Kazuhiko Tasaka It is certified that error appears in the above-identified patent and that said Letters Patent is hereby corrected as shown below:

In the Specification

Column 1, line 25, change "also refereed to as" to -- also referred to as --; and Column 15, line 63, change "24$f$Q," to -- 24$f$Q --.

Signed and Sealed this
Twelfth Day of May, 2015

Michelle K. Lee
*Director of the United States Patent and Trademark Office*